United States Patent [19]

Michna

[11] Patent Number: 4,906,190
[45] Date of Patent: Mar. 6, 1990

[54] DENTAL PROSTHESIS

[76] Inventor: Claus G. Michna, 4 Toby La., Brookfield Center, Conn. 06804

[21] Appl. No.: 255,494

[22] Filed: Oct. 11, 1988

[51] Int. Cl.⁴ .............................................. A61C 13/00
[52] U.S. Cl. .................................................... 433/175
[58] Field of Search ................ 437/173, 174, 175, 176

[56] References Cited

U.S. PATENT DOCUMENTS 3,343,263 9/1967 Henlotter ............................. 433/175
3,628,248 12/1971 Kroder et al. ..................... 433/201.1

Primary Examiner—Robert Peshock
Attorney, Agent, or Firm—Vincent A. Mallare

[57] ABSTRACT

A synthetic tooth for replacing an actual tooth by inserting a flexible crowned member into the socket of the removed tooth. The synthetic tooth is conformed to the tooth socket and filled to replace the actual tooth therein.

7 Claims, 5 Drawing Sheets

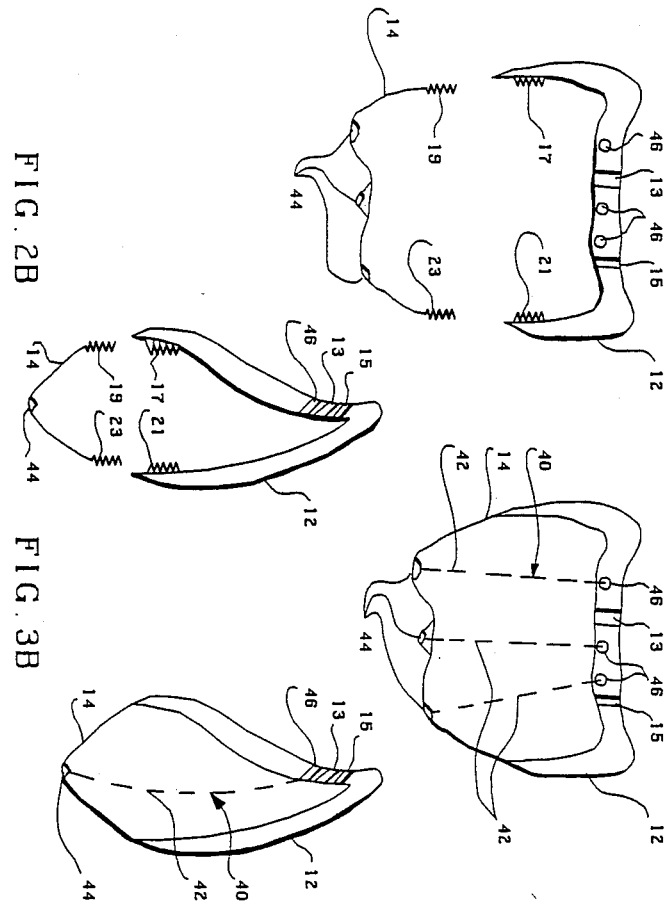

DENTAL PROSTHESIS

BACKGROUND OF THE INVENTION

This invention relates to teeth, and more particularly to a method for replacing natural teeth with synthetic teeth.

Generally, teeth consist of three regions: an exposed portion, the crown; a root, which embeds in the jawbone; and a slightly constricted neck at the gum level. The three layers of a tooth are the dentin, which makes up most of the tooth; a hard enamel, which covers the dentin of the crown; and the pulp, composed of connective tissue rich in nerves and blood vessels. These vessels and nerves enter and leave the tooth through the apical foramen. The periodontal membrane lines the tooth socket and secretes the bony cementum that holds the tooth in place.

When such teeth are removed and replaced, it is generally a lengthy and costly procedure in which the individual is usually without the use of any permanent teeth. The cost of such dental procedure is most times too expensive and those needing a tooth or teeth replaced have to go without or have inexpensive and, most times, insecure, sloppy-fitting teeth to replace their natural teeth.

Thus, it is an object of this invention to provide a means of replacing removed teeth with secure, effective teeth, in a short time, almost immediately, at little cost. These teeth effectively replace original teeth so that one ca be assured of good looking, strong teeth.

SUMMARY OF THE INVENTION

A method for installing a synthetic tooth composed of a crown and flexible plastic sack secured thereto that is arranged to fit securely in the socket of a removed tooth. The method comprises:

(a) heating the flexible sack to a state where such is able to be conformed with the walls of the tooth socket;

(b) placing the crown and heated sack over the socket;

(c) injecting air through a valve opening of the crown to expand the heated sack snugly in the socket;

(d) venting any air/liquid build-up in the bottom of the tooth socket; and (e) injecting a heated plastic material through a second crown valve opening to fill the sack and form a solid tooth in the socket, whereby the tooth is secure in the socket of the removed tooth.

DRAWINGS

The present invention will be better understood by considering the following drawings with the detailed description below. The drawings are:

FIGS. 2A and 2B illustrate, respectively, two-component, back and front, synthetic teeth according to the present invention;

FIGS. 3A and 3B illustrate, respectively, single-component back and front synthetic teeth according to the present invention;

DETAILED DESCRIPTION OF THE INVENTION

Figure 1:
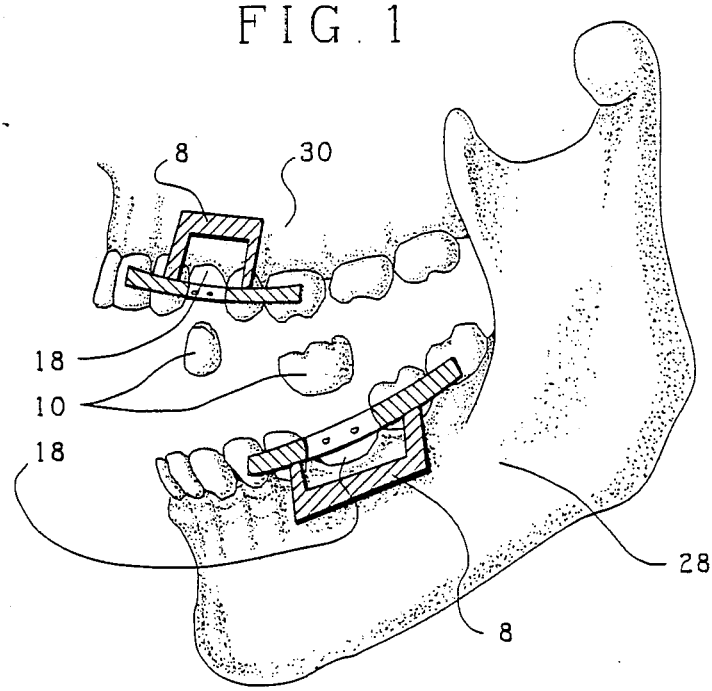
FIG. 1 is a perspective view of a clamp arranged around the socket into which a synthetic tooth will be placed according to the present invention.

The synthetic teeth of this invention are constructed in a way that renders them to have the same form as natural teeth with better durability and performance, and these synthetic teeth, according to the present invention, are able to be constructed and placed in the socket of a removed tooth with ease and in a very short period of time after the natural tooth is removed.

And, the cost for such procedure is at a substantial savings for the individual. The cost is generally about one-tenth the cost today for replacing a removed tooth. According to the present invention, an important and necessary feature for individuals is that they can have a fully effective tooth replacing the removed tooth in a fraction of the time needed today. The new functioning tooth may be placed securely within the socket in less than about one-half hour.

According to the present invention, the replacement tooth, i.e., the crown and sack to be conformed to the socket of the removed tooth is generally made in one process out of the same material. The crown and flexible sack may be made separately out of different materials and sealed together to be conformed and filled in the socket of the removed tooth. Also, it is intended by this invention that a removed tooth may be replaced long after it has been removed, as well as immediately after being removed. This may require some minor surgery by the dentist to remove the skin and flesh covering the socket of the removed tooth.

In the event the socket walls are damaged or the socket is too shallow, the socket may be opened wider and/or deeper with grooves in the socket wall by known dental procedures.

In the process of making a crown and flexible sack in one unit, a particular plastic material may be die-casted to form the crown and the flexible sack in one unit. AccordinglY, the crown is a thicker portion of this plastic material, whereas the flexible sack is a thinner portion of this material which can be heated to conform to the walls of the socket of the removed tooth.

When making the single-component, synthetic tooth, i.e., a crown and flexible sack, the open ends of the sack will be sealed and cut to be conformable with the socket of a removed tooth. Before the flexible sack has its cut-off ends sealed, an air/liquid venting means by its by its tubing and head is placed in the bottom of the sack and sealed.

According to the present invention, the flexible sack is preferably made out of a plastic material that can be heated to become flexible to conform with the socket of the removed tooth and when cooled, it will adhere to and be compatible with the socket walls.

As indicated above, the flexible sack, before being used, is cured with the crown in the die-cast. Just before use, the flexible sack is heated to be able to be conformed to the socket of the removed tooth.

The synthetic tooth made according to the present invention is comprised of a crown, a flexible sack securely sealed to the crown and filled with a plastic material to conform with any shape and form of a tooth socket.

Referring to FIG. 1, there is a socket (18) of a removed tooth where a clamp (8) is arranged around the socket (18) into which the synthetic tooth (10) is to be placed. As shown in FIG. i, the clamp (8) is attached to the teeth surrounding the socket (18) and the upper (30) or lower (28) jawbone.

Figure 4:
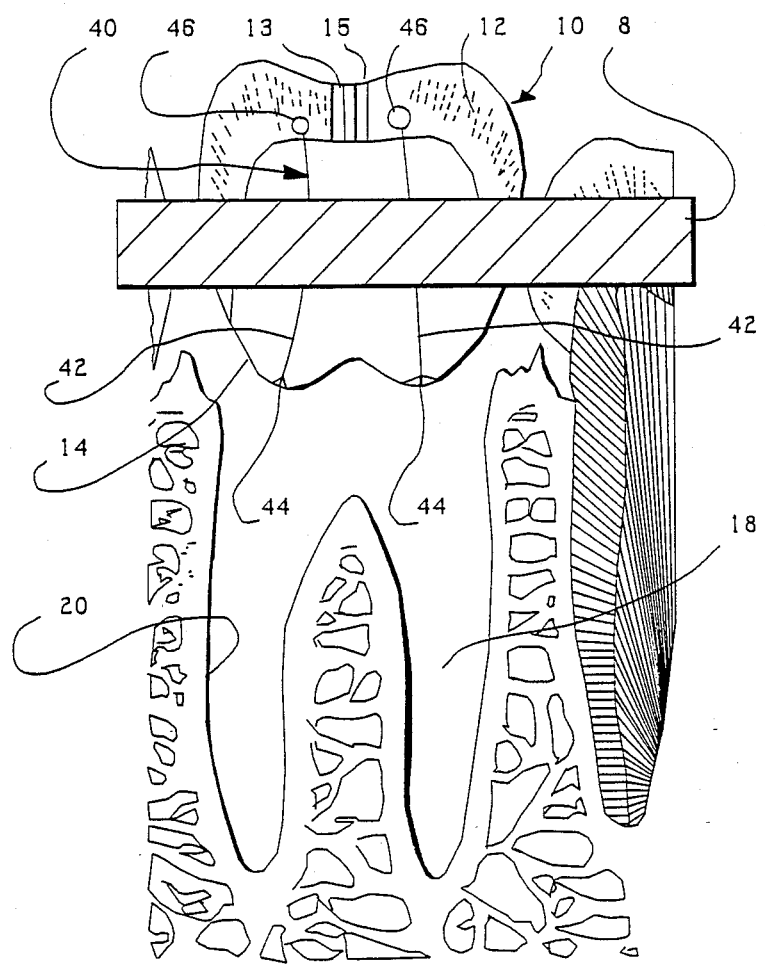
FIG. 4 is a side-elevational view of a synthetic tooth of the present invention positioned over the socket of a removed tooth.

As shown in FIG. 4, the crown (12) of the synthetic tooth (10) is secured within the clamp (8) after a satisfactory bite test is made for the tooth (10). In order to flex and conform the sack (14) with socket walls (20), the crown (12) has an air pressure intake control valve (13) for the air to flex and inflate the sack (14) and hold the air pressure until the sack (14) is hardened.

Figure 5:
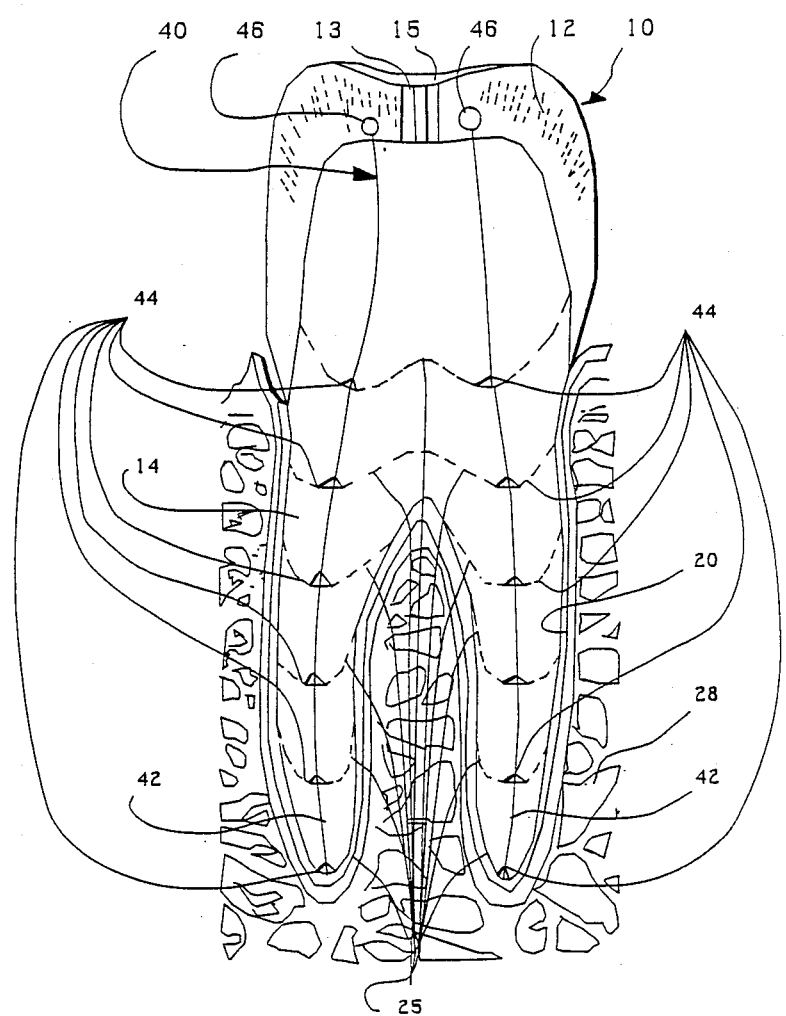
FIG. 5 is an elevational view of the sYnthetic tooth of FIG. 4 illustrating the flexible sack and its air/liquid venting means, and where the flexible sack is being expanded in various degrees to conform with the socket of the removed tooth.
Figure 6:
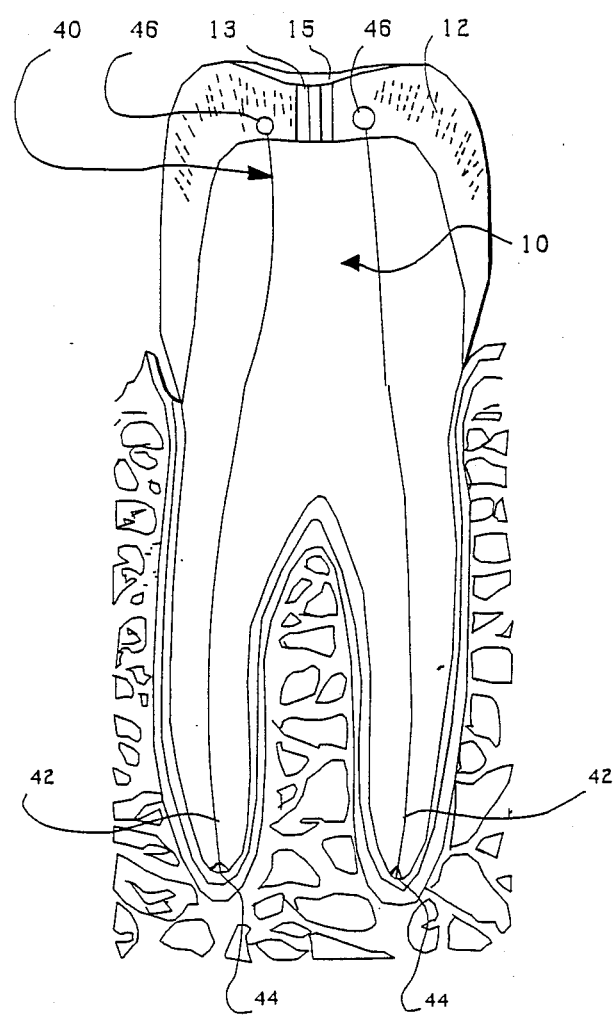
FIG. 6 is an elevational view of the synthetic tooth of FIGS. 4 and 5 fully constructed and secured in the socket of the removed tooth.

In order to prevent the air pressure and liquid build-up in the bottom of the tooth socket, it is necessary to provide the flexible sack and tooth with an air/liquid venting means as shown in FIGS. 4, 5, and 6.

As shown in FIGS. 4, 5, and 6, the air/liquid venting means (40) includes for each root of the removed tooth a tubing (42) having a head (44) sealed in the bottom of the sack (14), and a tubing opening.

After the sack (14) is hardened, the overflow valve (15) is opened to release the air. Then, a liquid plastic material is funneled through the control valve (13) to fill entirely the hardened sack (14). The overflow plastic material exits through the overflow valve (15).

After the air and liquid build-up has been vented, the tubing (42) is temporarily plugged, and then, when the tooth socket is satisfactory to the dentist, the tubing is permanently sealed in a manner similar to a root canal.

The tubing (42) may be made of any suitable plastic material.

Referring to FIG. 5, the heated flexible sack (14) is expanded and inflated by air pumped through the control valve (13). As shown by the expansion lines (25), the sack (14) is inflated and expanded to conform with the socket and walls (20) of the removed tooth.

As shown in FIGS. 2A and 2B, the teeth used in the present procedure may be a two-component unit in which the flexible sack (14) and crown (12) are made of different materials and secured together at points (17), (19), (21) and (23).

The crown (12) may be made of a material selected from the group consisting of a plastic, iron, gold, silver, titanium, and porcelain. And, the flexible sack may be made out of any plastic material which can be expanded to fill all sockets of removed teeth, securely adhere to the walls of the sockets, and which is compatible with the walls of the sockets of the removed tooth.

The tooth (10) of FIG. 2A may be used to replace removed molars, whereas the tooth (10) of FIG. 2B may be used for incisor and canine teeth.

The teeth shown in FIGS. 3A and 3B are examples of teeth that are a one-component unit that may be used to replace, respectively, molars and incisors. The teeth of FIGS. 3A and 3B may be made of the same material for both the crown (12) and sack (14).

As indicated bY FIG. 6, after the liquid plastic has hardened and set in the sack (14) of the tooth, the clamp (8) is removed. The overflow from valve (15) is ground off and the intake valve (13) is filled and both areas are smoothed down and polished to conform with the rest of the tooth.

According to the present invention, the synthetic tooth described herein maY be treated as, and will perform as well as, if not better, than the natural tooth it will replace. That is, the tooth may be ground, cleaned, polished, reworked with plastic materials, and will be stronger and less destructible than a natural tooth.

The teeth (i.e., crown and sack) of this invention may be made of any material that is approved by the Dental Society. The flexible sack should be made of a material that is flexible, able to set on cooling, and one that is compatible with the walls of the tooth socket.

I claim:

1. A synthetic tooth comprised of a crown, a flexible sack securely sealed to said crown and filled with a plastic material to conform with any shape and form of a tooth socket, said sack being hardened when conformed to said socket and includes an air/liquid venting means, whereby the air pressure and liquid build-up in the space between the sack and bottom of the tooth socket are vented.

2. The synthetic tooth of claim 1, wherein the flexible sack is composed of a material which can be expanded to fill all sockets of removed teeth and securely adhere to the walls of the sockets.

3. The synthetic tooth of claim 1, wherein the flexible sack is composed of a material that is compatible with the walls of the socket.

4. The synthetic tooth of claim 1, wherein said crown and flexible sack are composed of the sam material.

5. The synthetic tooth of claim 1, wherein the crown is made of a material selected from the group consisting of a plastic, iron, gold, silver, titanium, and porcelain.

6. The synthetic tooth of claim 1, wherein the air/liquid venting means comprise flexible tubings each having a head sealed in bottom of said flexible sack and tube openings for each tube in said crown.

7. A method for preparing a synthetic tooth composed of a crown and flexible sack secured thereto, that is arranged to fit securely in the socket of a removed tooth, said method comprising:
  (a) heating said flexible sack to a state where such is able to be conformed with the walls of the tooth socket and thereafter hardened on cooling;
  (b) placing said crown and heated sack over said socket;
  (c) injecting air through an opening of said crown to expand said heated sack snugly in said socket;
  (d) venting any air/liquid build-up in the bottom of the tooth socket; and
  (e) injecting a heated plastic material through a crown opening to fill said sack and form a hardened tooth in said socket, whereby said tooth is secure in the socket of the removed tooth.

* * * * *